United States Patent [19]

Crawley et al.

[11] Patent Number: 4,900,657

[45] Date of Patent: Feb. 13, 1990

[54] NOVEL PYRAZOLONE PHOTOGRAPHIC COLOR COUPLERS AND PHOTOGRAPHIC ELEMENTS CONTAINING THEM

[75] Inventors: Michael W. Crawley, Kingswood; Paul Louis R. Stanley, Wealdstone, both of Great Britain

[73] Assignee: Eastman Kodak Company, Rochester, N.Y.

[21] Appl. No.: 358,047

[22] Filed: May 30, 1989

[30] Foreign Application Priority Data

Jun. 21, 1988 [GB] United Kingdom ............... 8814677

[51] Int. Cl.$^4$ .............................................. G03C 7/38
[52] U.S. Cl. ..................................... 430/555; 430/544
[58] Field of Search ............... 430/555, 544, 554, 957

[56] References Cited

U.S. PATENT DOCUMENTS

| 3,227,554 | 1/1966 | Barr et al. | 430/553 |
| 4,199,361 | 4/1980 | Furutachi | 430/554 |
| 4,351,897 | 9/1982 | Aoki et al. | 430/555 |
| 4,556,630 | 12/1985 | Furutachi et al. | 430/555 |
| 4,584,266 | 4/1986 | Hirose et al. | 430/555 |

Primary Examiner—Richard L. Schilling
Attorney, Agent, or Firm—Thomas F. Kirchoff

[57] ABSTRACT

Pyrazolone magenta dye-forming couplers are described which provide excellent formaldehyde stability and which result in dyes having good stability to light, heat and moisture and which have higher $\beta$max values as compared with dyes obtained from prior described pyrazolone couplers.

5 Claims, No Drawings

NOVEL PYRAZOLONE PHOTOGRAPHIC COLOR COUPLERS AND PHOTOGRAPHIC ELEMENTS CONTAINING THEM

This invention relates to novel pyrazolone photographic color couplers and photographic elements containing them.

It is well established in the photographic art that color images may be obtained from imagewise exposed silver halide emulsions by developing them with a primary aromatic amine color developing agent in the presence of a color coupler. The oxidized color developing agent formed in the areas of silver halide development couples with the coupler to form a dye. the coupler may be present in the developer solution but is normally incorporated in the sensitive photographic material.

It is known that pyrazolones having a coupling-off group in the 4-position behave as 2-equivalent couplers producing approximately one mole of dye for every two equivalents of silver produced during color development. Among the coupling-off groups known in this connection are the arylthio groups as described, for example, in U.S. Pat. Nos. 3,227,554, 4,351,897, 4,556,630 and 4,584,266.

British Specification 1,552,701 describes pyrazolone couplers having a 1-pentahalogenophenyl substituent. While it is said that couplers having a 3-anilino group form dyes having longer λmax, of the specific couplers of this type exemplified none has a λmax greated than 543 nm.

Among the above known couplers there is none which has all the properties required to produce a commercially acceptable photographic color material, in particular a color negative film material.

Accordingly there is provided a pyrazolone color coupler of the general formula:

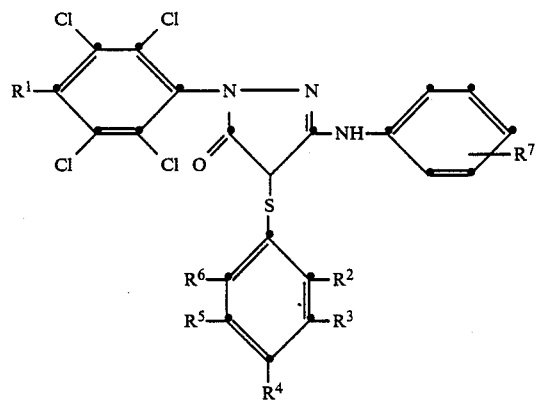

wherein:

$R^1$ is H or Cl;

$R^2$ is $NHSO_2R^9$, $NHCOR^9$, $—NHCONHR^9$, $—CONHR^9$, $—NR^8R^9$, $—R^9$ or $—OR^9$, or together with $R^3$ forms a fused ring system;

$R^3$, $R^4$, $R^5$ and $R^6$ are each H, Cl or as described for $R^2$;

$R^7$ is H, $—COOR^8$ or $—CONHR^8$;

$R^8$ is alkyl or substituted alkyl; and $R^9$ is H or as defined for $R^8$.

Couplers used in the present invention have excellent formaldehyde stability, keeping properties and coupling activity and provide image dyes of the desired hue having good stability to light, heat and mositure.

Examples of alkyl groups which $R^8$ may represent include those having from 1 to about 20 carbon atoms, especially from 1 to about 4 carbon atoms, such as methyl, ethyl, n-propyl, iso-propyl, n-butyl, t-butyl. Higher alkyl groups having from about 12 to about 20 carbon atoms are also useful. Such alkyl groups may be substituted, for example, with halogen atoms, alkoxy, hydroxy, carboxylic acid and aryl groups.

A preferred $R^5$ substituent is alkyl having from about 8 to about 15 carbon atoms. The $R^7$ substituent in the anilino ring can be a ballast group. Preferred ballast groups comprise from about 12 to about 15 carbon atoms linked to the ring through a —COO— or a —NHCO— group at the 3 or 4 position.

Specific examples of couplers according to the present invention are illustrated in the following table:

TABLE I

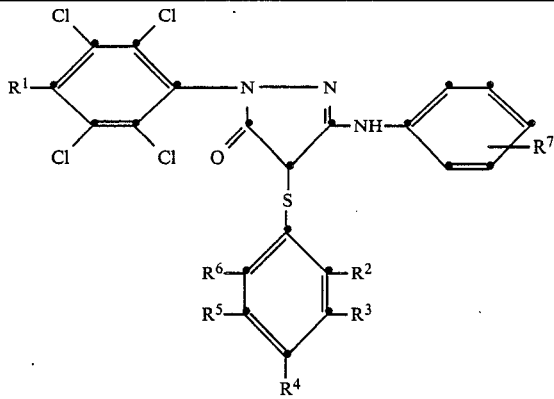

| Coupler Number | $R^1$ | $R^2$ | $R^3$ | $R^4$ | $R^5$ | $R^6$ | $R^7$ | λmax | HBW, nm |
|---|---|---|---|---|---|---|---|---|---|
| 1 | Cl | n-BuO | H | H | t-Oct | H | 3-NHCO$_{15}$H$_{31}$ | 550.0 | 80.5 |
| 2 | Cl | t-Bu | H | H | H | H | " | 552.5 | 82.5 |
| 3 | Cl | t-Bu | H | H | C$_{15}$H$_{32}$—n | H | " | 552.5 | 81.0 |
| 4 | Cl | n-BuO | H | H | t-Oct | H | 3-NHCO—R$^{10}$* | 553.5 | 85.0 |
| 5 | Cl | t-Bu | H | H | C$_{15}$H$_{31}$—n | H | " | 553.5 | 84.0 |
| 6 | Cl | i-Pr | H | i-Pr | H | i-Pr | " | 554.5 | 85.5 |
| 7 | Cl | i-Pr | H | i-Pr | H | i-Pr | 4-COOC$_{12}$H$_{25}$ | 548.0 | 83.5 |
| 8 | Cl | ** | ** | ** | ** | ** | " | 551.0 | 81.0 |
| 9 | Cl | t-Bu | H | H | H | H | " | 549.0 | 82.0 |
| 10 | Cl | —NHSO$_2$Me | H | H | H | H | " | 550.0 | 79.0 |
| 11 | Cl | i-Pr | H | i-Pr | H | H | " | 549.0 | 82.5 |
| 12 | Cl | —N(Me)$_2$ | H | H | H | H | " | 549.0 | 80.0 |
| 13 | Cl | —NHCOBu—t | H | H | H | H | " | 549.5 | 80.0 |
| 14 | Cl | Me | H | Me | H | Me | " | 548.5 | 82.0 |
| 15 | Cl | t-Bu | H | Cl | H | H | " | 549.0 | 82.0 |
| 16 | Cl | n-BuO | H | H | t-Oct | H | 3-COOC$_{12}$H$_{25}$—n | 548.5 | 81.0 |
| 17 | Cl | n-BuO | H | H | t-Oct | H | 4-COOC$_{12}$H$_{25}$—n | 546.0 | 80.5 |
| 18 | Cl | i-Pr | H | i-Pr | H | i-Pr | 3-COOC$_{12}$H$_{25}$—n | 546.0 | 81.0 |
| 19 | H | n-BuO | H | H | t-Oct | H | 3-NHCOC$_{15}$H$_{31}$—n | 547.0 | 80.5 |

*$R^{10}$ is 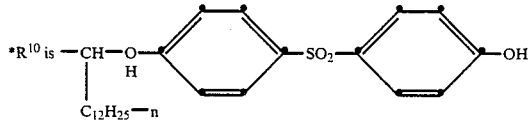

**the coupling off group is 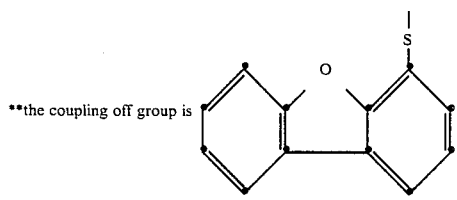

The instant couplers may be prepared from their 4-equivalent parent couplers by the methods illustrated in the following preparations.

Preparation 1—Coupler 3

2-t-Butyl-5-n-pentadecylthiophenol (4.5 g, 12 mmol) was dissolved in dichloromethane (10 ml) and sulphuryl chloride (1.6 g, 12 mmol) added. The mixture was stirred at room temperature for 30 minutes and the solvent removed (40° C.) by rotary evaporation to give the sulphenyl chloride as a red oil. A solution of the 4 equivalent parent couplers (7.1 g, 10 mmol) in dimethylformamide (20 ml) was rapidly added to the oil and stirred at 40° C. for 2 hours and then at room temperature overnight. The solution was poured into stirred, dilute hydrochloric acid (200 ml) and the solid filtered off, washed with water and triturated with acetone (300 ml) to give the product as a fine white powder, 10.4 g, 96%. HPLC analysis indicated a purity of 98%+. Req: C 61.9, H 7.4, Cl 19.6, N 5.2, S 2.95. Fd: C 61.8, H 7.4, Cl 19.3, N 5.4, S 3.2.

Preparation 2—Coupler 13

The 4-equivalent parent coupler (51.0 g, 76.1 mmol) and bis[2-(t-butylcarbamoyl)phenyl]-disulphide (19.0 g, 45.7 mmol) were dissolved in dimethylformamide (600 ml) and bromine (7.3 g, 45.8 mmol) added dropwise with stirring at room temperature. The resulting mixture was heated at 60° C. over 2 hours and then stirred at room temperature overnight. The reaction mixture was poured into dilute hydrochloric acid (101) and the solid filtered off, washed and dried. Flash chromatography using ethyl acetate and 60°-80° C. petrol (1:2) gave the major fraction containing the product which was crystallized from ethyl acetate: petrol (1:3) to give the pure coupler 241HJA as a white solid, 46.2 g, 69%. HPLC analysis indicated the product was 99% pure.

Req: C 53.4, H 5.05, Cl 24.2, N 6.4, S 3.65. Fd: C 53.7, H 5.0, Cl 24.1, N 6.5, S 3.5.

The dye-forming couplers of this invention can be used in the ways and for the purposes that dye-forming couplers have been previously used in the photographic art.

Typically, the couplers are associated with a silver halide emulsion layer coated on a support to form a photographic element. As used herein, the term "associated therewith" signifies that the coupler is incorporated in the silver halide emulsion layer or in a layer adjacent thereto where, during processing, it is capable of reacting with silver halide development products.

The photographic elements can be single color elements or multicolor elements. In a multicolor element, the magenta dye-forming couplers of this invention would usually be associated with a green-sensitive emulsion, although they could be associated with an emulsion sensitized to a different region of the spectrum, or with a panchromatically sensitized, orthochromatically sensitized or unsensitized emulsion. Multicolor elements contain dye image-forming units sensitive to each of the three primary regions of the spectrum. Each unit can be comprised of a single emulsion layer or of multiple emulsion layers sensitive to a give region of the spectrum. The layers of the element, including the layers of the image-forming units, can be arranged in various orders as known in the art.

A typical multicolor photographic element comprises a support bearing yellow, magenta and cyan dye image-forming units comprising at least one blue-, green- or red-sensitive silver halide emulsion layer having associated therewith at least one blue-, green- or red-sensitive silver halide emulsion layer having associated therewith at least one yellow, magenta or cyan dye-forming coupler respectively, at least one of the magenta dye-forming couplers being a coupler of this invention. The element can contain additional layers, such as filter and barrier layers.

In the following discussion of suitable materials for use in the emulsions and elements of this invention, reference will be made to Research Disclosure, December 1978, Item 17643, published by Industrial Opportunities Ltd., The Old Harbour-master's, 8 North Street, Emsworth, Hants P010 7DD, U.K. This publication will be identified hereafter as "Research Disclosure".

The silver halide emulsion employed in the elements of this invention can be either negative-working or positive-working. Suitable emulsions and their preparation are described in Research Disclosure Sections I and II and the publications cited therein. Suitable vehicles for the emulsion layers and other layers of elements of this invention are described in Research Disclosure Section IX and the publications cited therein.

In addition to the couplers of this invention, the elements of the invention can include additional couplers as described in Research Disclosure Section VII, paragraphs D, E, F and G, and the publications cited therein. The couplers of this invention and any additional couplers can be incorporated in the elements and emulsions as described in Research Disclosures of Section VII, paragraph C and the publications cite therein.

The photographic elements of this invention or individual layers thereof, can contain brighteners (see Research Disclosure Section V), antifoggants and stabilizers (see Research Disclosure Section VI), antistain agents and image dye stabilizer (see Research Disclosure Section VII, paragraphs I and J), light absorbing and scattering materials (see Research Disclosure Section VIII), hardeners (see Research Disclosure Section XI), plasticizers and lubricants (see Research Disclosure Section XII), antistatic agents (see Research Disclosure Section XIII), matting agents (see Research Disclosure Section XVI) and development modifiers (see Research Disclosure Section XXI).

The photographic elements can be coated on a variety of supports as described in Research Disclosure Section XVII and the references described therein.

Photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

Preferred color developing agents are p-phenylene diamines. Especially preferred are 4-amino-3-methyl-N,N-diethylaniline hydrochloride, 4-amino-3-methyl-N-ethyl-N-$\beta$-(methanesulphonamido)-ethylaniline sulphate hydrate, 4-amino-3-methyl-N-ethyl-N-$\beta$-hydroxyethylaniline sulphate, 4-amino-3-$\beta$-(methanesulphonamido)ethyl-N,N-diethylaniline hydrochloride and 4-amino-N-ethyl-N-(2-methoxyethyl)-m-toluidine di-p-toluene sulphonate.

With negative-working silver halide emulsions this processing step leads to a negative image. To obtain a positive (or reversal) image, this step can be preceded by development with a non-chromogenic developing agent to develop exposed silver halide, but not form dye, and then uniform fogging of the element to render unexposed silver halide developable. Alternatively, a direct positive emulsion can be employed to obtain a positive image.

Development is followed by the conventional steps of bleaching, fixing, or bleach-fixing, to remove silver and silver halide, washing and drying.

The following Examples are given for a better understanding of the invention. All temperatures are in °C.

Example 1—Hue advantage

Coatings of the following format were made, coating weights are in g/m$^2$:

| | |
|---|---|
| Gelatin Overcoat | (1.5) |
| Green sensitized silver bromoiodide emulsion | (1.61) |
| Coupler | (1.04 mmol/m$^2$) |
| Gelatin | (2.42) |
| Bis methylvinyl sulphone (hardener) | (0.06) |
| / / / Cellulose acetate support / / / | |

The coupler (8.8 g) was dispersed in a mixture of dibutylphthalate and methylethyl ketone (2:1 by volume) with gelatin (6.0 g) as the continuous phase.

The strips were sensitometrically exposed and processed through the C41 process.

Couplers of the present invention were compared with equivalent trichloro couplers with regard to the hue of the dye produced when processed in the process described in the British Journal of Photography Annual, 1988, pp. 196–197.

TABLE 2

| Coupler No. | λmax (penta) | λmax (tri) |
|---|---|---|
| 6 | 554.5 | 546.0 |
| 4 | 553.5 | 544.5 |
| 5 | 553.0 | 544.0 |

In each cast there is a bathochromic shift to a more desirable region of the spectrum for the couplers of the invention.

Example 2—Formaldehyde Resistance

Strips of coated coupler prepared as in Example 1 were exposed for two days to formaldehyde at 60% RH. The treated strips together with control strips were processed as described in Example I to yield dye-containing strips whose density was measured. Table 3 below shows density values for couplers of this invention and their corresponding 4-equivalent parent couplers:

TABLE 3

| Coupler Number | % Density loss (invention) | % Density loss (parent) |
|---|---|---|
| 1 | −1.1 | 75.1 |
| 2 | −6.0 | " |
| 3 | −0.1 | " |
| 7 | 1.4 | 28.4 |
| 8 | 3.0 | " |
| 9 | 0.0 | " |
| 10 | −1.7 | " |
| 11 | −1.7 | " |
| 12 | −3.8 | " |
| 14 | −3.7 | " |
| 15 | 4.6 | " |
| 16 | 4.0 | " |

TABLE 3-continued

| Coupler Number | % Density loss (invention) | % Density loss (parent) |
|---|---|---|
| 17 | −0.4 | 31.1 |
| 18. | 14.8 | " |

A negative sign indicates a density gain. The results show that exposure to formaldehyde has considerably less effect on couplers of the invention compared to their parent couplers.

Example 3—Comparison with Prior Art Couplers

Test coatings were prepared as in Example 1. The coated strips were sensitometrically exposed and processed as described in Example I. The comparison couplers A, B, C represent prior art commercially used couplers. The results are recorded in Table 4.

TABLE 4

| Coupler Number | $\lambda_{max}$ | HBW | $D_{max}$ | λ |
|---|---|---|---|---|
| 3 | 551.0 | 80.0 | 3.09 | 3.50 |
| 13 | 549.5 | 79.5 | 3.01 | 3.20 |
| 19 | 547.0 | 80.5 | 2.78 | 3.24 |
| A | 541.5 | 83.5 | 2.74 | 3.68 |
| B | 548.0 | 94.5 | 2.87 | 3.98 |
| C | 554.5 | 96.5 | 2.30 | 2.01 |

The prior art couplers have the formulae:

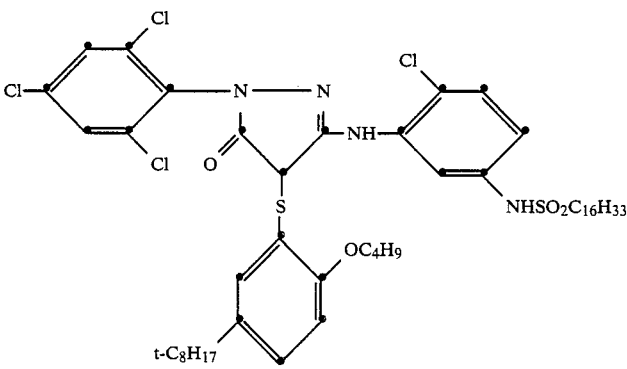

(A)

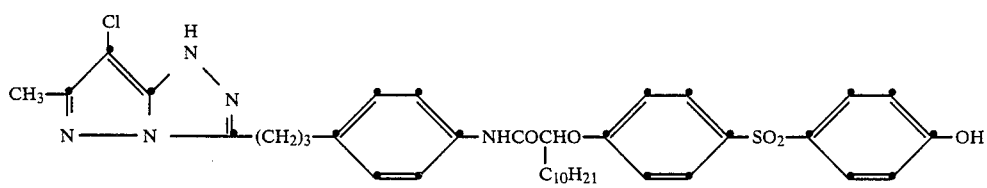

(B)

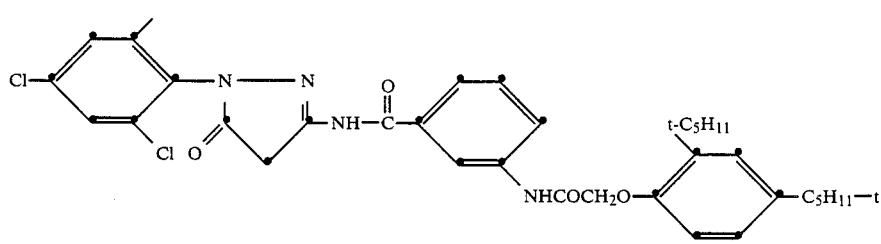

(C)

As can be seen from the above results the couplers of the present invention provide image dyes at the desired higher λmax and have narrower half bandwidth values than do dyes of the prior art. $D_{max}$ and γ values are both within the desired range.

This invention has been described in detail with particular reference to preferred embodiments thereof, but will be understood that variations and modifications can be effected within the spirit and scope of the invention.

We claim:

1. A photographic recording material comprising a support and a photosensitive silver halide emulsion layer which has associated therewith a magenta dye-forming coupler compound having the structural formula:

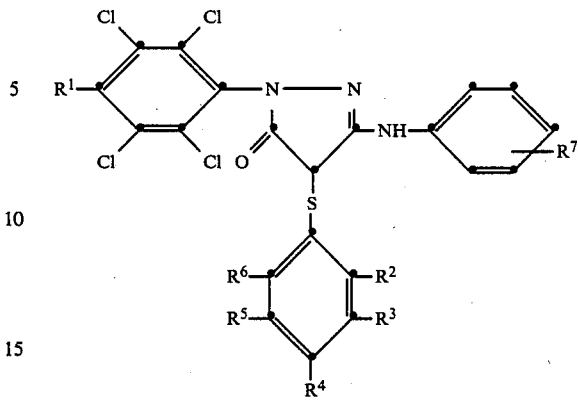

wherein:
$R^1$ is H or Cl;
$R^2$ is $NHSO_2R^9$, $NHCOR^9$, $-NHCONHR^9$, $-CONHR^9$, $-NR^8R^9$, $-R^9$ or $-OR^9$, or together with $R^3$ forms a fused ring system;
$R^3$, $R^4$, $R^5$ and $R^6$ are each H, Cl or $R^2$;
$R^7$ is H, $-COOR^8$ or $-CONHR^8$;
$R^8$ is alkyl or substituted alkyl; and
$R^9$ is H or as defined for $R^8$.

2. The photographic material of claim 1 wherein $R^2$ is an alkyl or an alkoxy group having 1 to about 4 carbon atoms.

3. The photographic material of claim 1 wherein $R^5$ is an alkyl group having from about 8 to about 15 carbon atoms.

4. The photographic material of claim 1 wherein $R^7$ comprises a ballast group having from about 12 to about 15 carbon atoms linked to the anilide ring through a $-COO-$ or a $-NHCO-O$ group at the 3 or 4 position.

5. The photographic material of claim 1 wherein $R^1$ is chloro.

* * * * *

UNITED STATES PATENT AND TRADEMARK OFFICE
CERTIFICATE OF CORRECTION

PATENT NO. : 4,900,657
DATED : February 13, 1990
INVENTOR(S) : M W. Crawley et al.

It is certified that error appears in the above-identified patent and that said Letters Patent is hereby corrected as shown below:

Title page:

Abstract, line 4, "βmax" should be —λmax—.

Col. 5, line 25, "give" should be —given—.

Col. 5, line 62, "cite" should be —cited—.

Col. 9, line 8, after "but" add —it—.

Col. 10, line 37, "-NHCO-0" should be — -NHCO- —.

Signed and Sealed this

Twentieth Day of August, 1991

*Attest:*

*Attesting Officer*

HARRY F. MANBECK, JR.

Commissioner of Patents and Trademarks